United States Patent [19]

Steffin

[11] 4,441,507

[45] Apr. 10, 1984

[54] HIGH SPEED SINGLE ELECTRODE MEMBRANE VOLTAGE CLAMP

[76] Inventor: Morris Steffin, 27 Bell Canyon Rd., Bell Canyon, Calif. 91370

[21] Appl. No.: 325,977

[22] Filed: Nov. 30, 1981

[51] Int. Cl.³ .............................................. A61B 5/04
[52] U.S. Cl. .................................................. 128/734
[58] Field of Search ............... 128/630, 639, 642, 734, 128/902

[56] References Cited

U.S. PATENT DOCUMENTS 4,240,443 12/1980 Ionesco ............................ 128/234

OTHER PUBLICATIONS

Park et al., "Single Electrode Voltage Clamp . . . " J. of Neuroscience Methods, 3/81.
Johnston et al., "Voltage Clamp . . . Neurones", Nature, 7/80.
Kootsey et al., "Buffer Amplifier . . . ", IEEE Trans BME, Sep. 1973.
Wilson et al., "Voltage Clamping . . . Single Microelectrode", J. of Neurobiology, vol. 6, No. 4, pp. 411–422.
Merickel, "Design of Single Electrode Voltage Clamp", J. Neuroscience Method, 2/80, 87–96.
Jochem et al., "A High Voltage Electrometer . . . ", J. Neuroscience Methods 3/81, 261–269.
Zoble et al., "Automated On-Line . . . Curves", IEEE Trans. BioMed. Eng., vol. BME 25, No. 5, Sep. 1978, 481–483.

Primary Examiner—Lee S. Cohen
Attorney, Agent, or Firm—Spensley, Horn, Jubas & Lubitz

[57] ABSTRACT

A high speed single electrode voltage clamp circuit for enabling study of the action potentials in small and otherwise inaccessible nerve cells. The circuit includes a high input impedance, low input capacity input stage, a high frequency emphasis equalization network, and separate low frequency and transient compensation networks and spectral modification circuitry. In addition, computer correction is utilized to eliminate transient errors. Proper operation of the clamp is also monitored by means of a computer.

23 Claims, 21 Drawing Figures

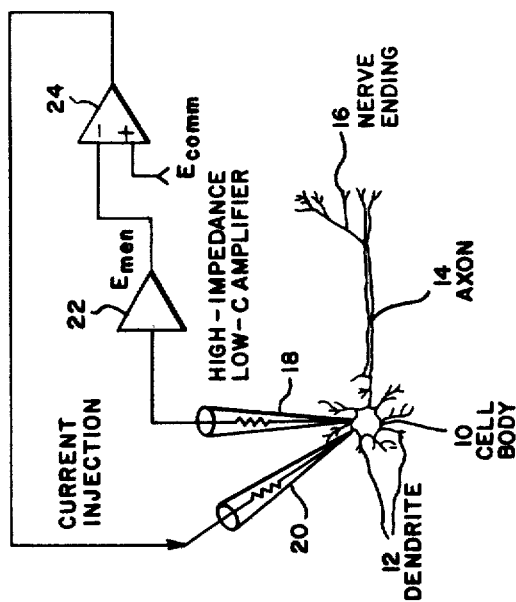
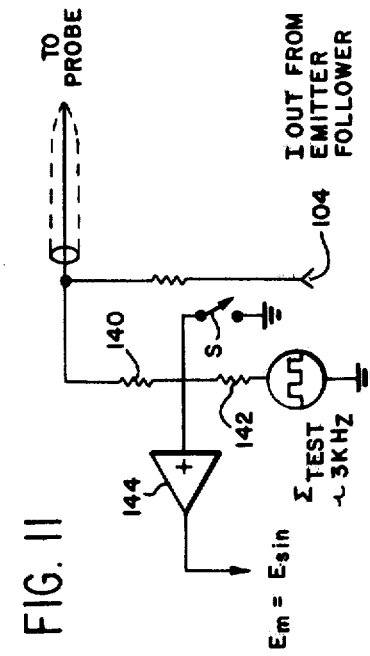
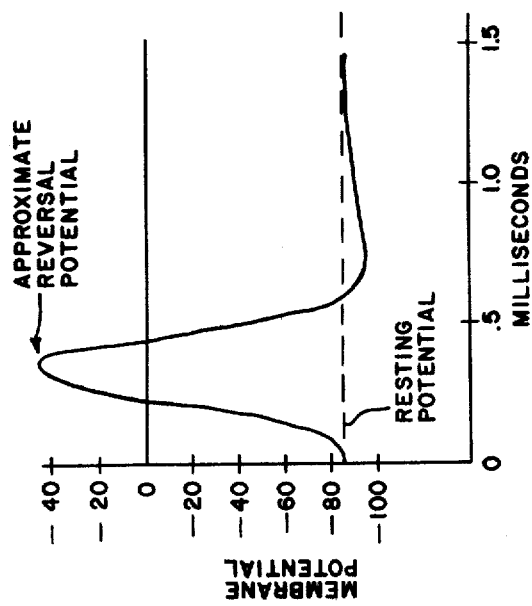
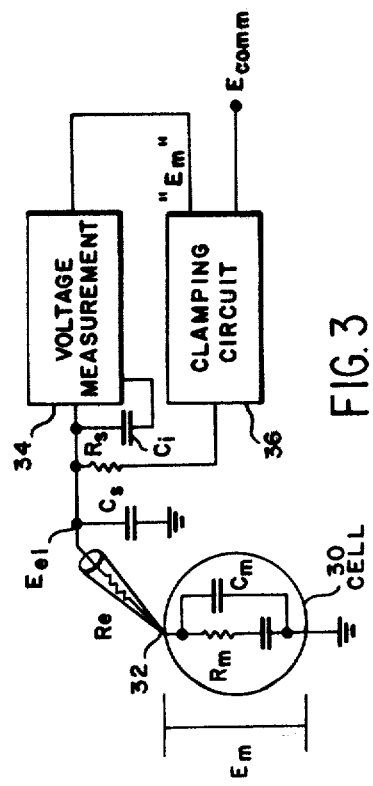
FIG. 1
FIG. 2 (PRIOR ART)
FIG. 3
FIG. 11

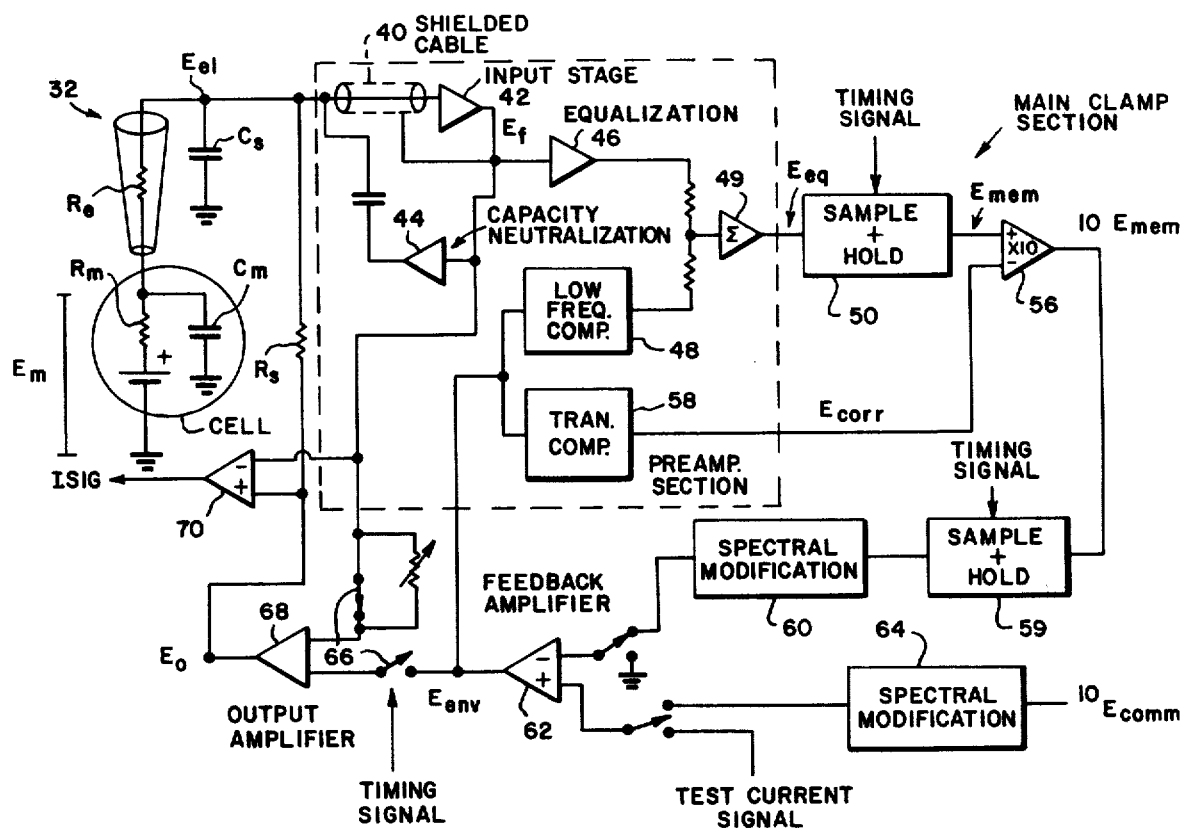
FIG.5
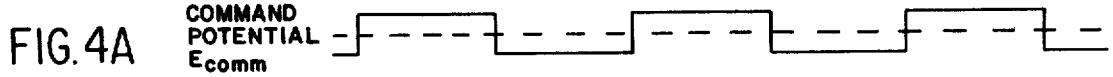
FIG.4A — COMMAND POTENTIAL $E_{comm}$
FIG.4B — $E_{el} = E_f$ (W/O FEEDBACK)
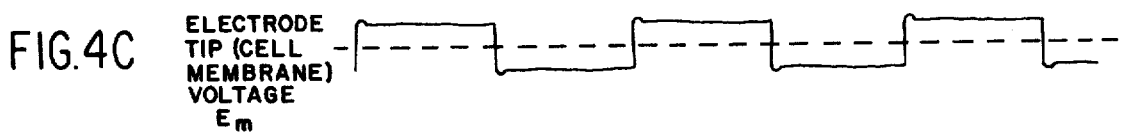
FIG.4C — ELECTRODE TIP (CELL MEMBRANE) VOLTAGE $E_m$
FIG.4D — $E_{el} = E_f$ (WITH FEEDBACK)

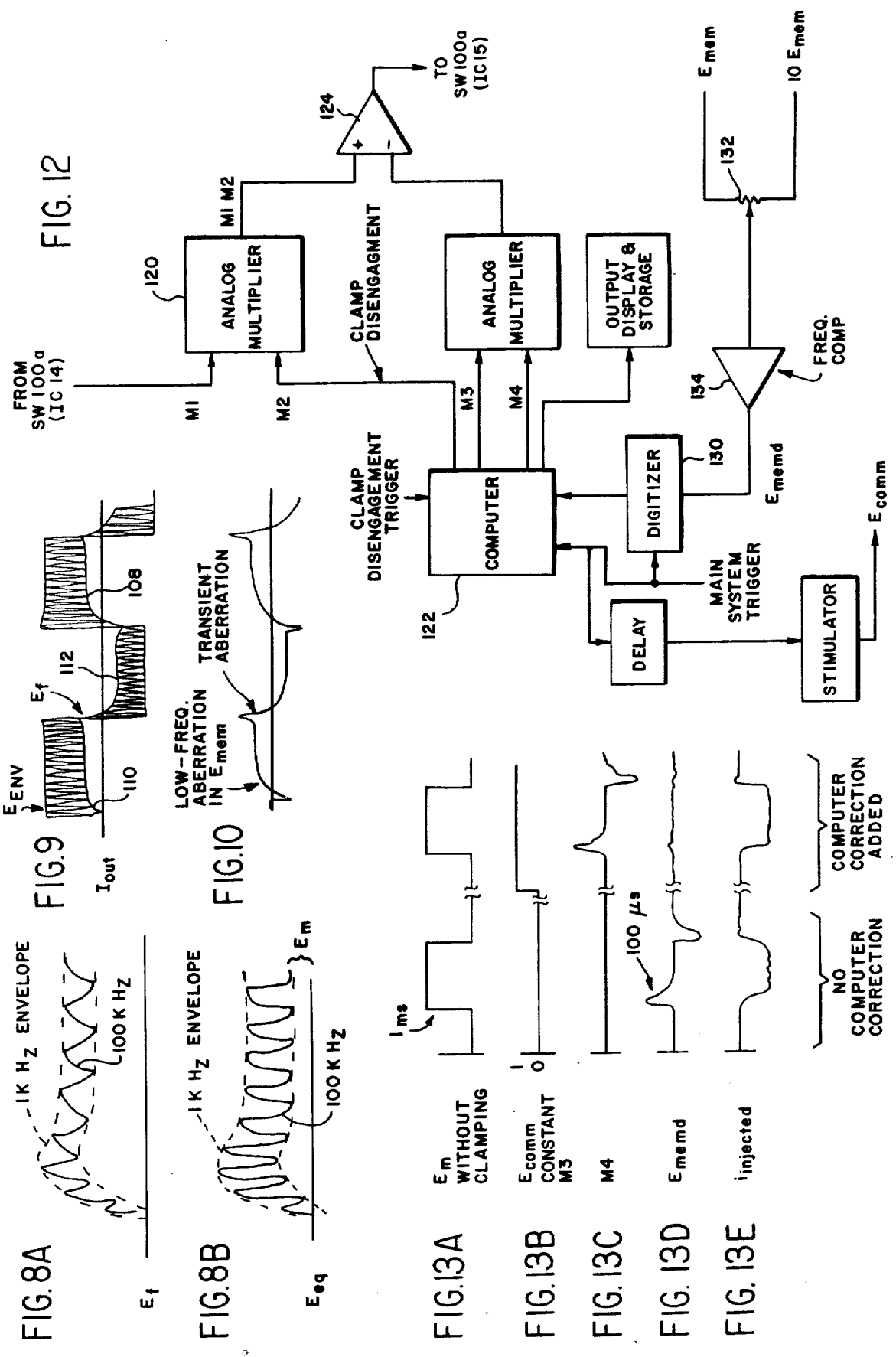

HIGH SPEED SINGLE ELECTRODE MEMBRANE VOLTAGE CLAMP

BACKGROUND OF THE INVENTION

1. Field of the Invention

This invention relates to the study of electrical activity of cells, and in particular the activity of nerve cells. Electrical potentials exist across the membranes of essentially all cells of the body, and some cells, such as nerve and muscle cells, are "excitable"—that is, capable of transmitting electrochemical impulses along their membranes.

The fluids located both inside and outside of nerve cells are electrolytic solutions. Generally, an excess number of negative ions accummulates immediately inside the cell membrane, and an equal number of positive ions accummulates immediately outside the membrane. The result of this is the development of what is known as a transmembrane potential. The transmembrane potential is believed to be primarily caused by the sodium "pump" in which positively charged sodium ions are transported to the exterior of the cell. Once the concentration of sodium outside the nerve cell has reached a particular value, sodium leaks back to the inside of the cell as rapidly as it is being pumped out, thus developing a state of equilibrium. Equilibrium occurs when the interior of the cell is approximately −85 millivolts with respect to the exterior of the cell.

So long as the membrane of the nerve cell remains completely undisturbed, the membrane potential remains at approximately −85 millivolts. This is called the resting potential. However, any factor that suddenly increases the permeability of the membrane to sodium is likely to elicit a sequence of rapid changes in membrane potential lasting a small fraction of a second, followed immediately by return of the membrane potential to its resting value. This sequence of changes in membrane potential is called the action potential.

Some of the factors that can elicit an action potential are electronic stimulation of the membrane, application of chemicals to the membrane to cause increased permeability to sodium, heat, cold or almost any other factor that momentarily disturbs the normal resting state of the membrane.

The action potential occurs in two separate stages called depolarization and repolarization. When the permeability of the cell membrane to sodium ions suddenly increases, many of the sodium ions rush to the inside of the cell, carrying enough positive charges to the inside to cause complete disappearance of the normal resting potential and usually enough charges to actually develop a positive state inside the cell instead of its normal negative state. This action is called depolarization and the positive state inside the cell is referred to as the reversal potential. Almost immediately after depolarization takes place, the pores of the cell membrane again become almost totally impermeable to sodium ions. Because of this, and because of potassium efflux resulting from an increase in potassium permeability, the reversal potential inside the cell disappears and the normal resting membrane potential returns. This is called repolarization. The change in membrane potential as the membrane permeability changes is shown in FIG. 1.

In order to study changes in membrane conductance, feedback circuits known as voltage clamps are utilized. Typically, the clamp will pass a variable current through the cell membrane such that the membrane voltage changes according to a preselected command voltage pattern in spite of changes of membrane conductance with voltage and time. The current is recorded and is used to compute membrane conductance at various voltage levels. By resolving changes in membrane conductance during excitation, especially conductance of sodium and potassium, the clamp allows resolution of subtle changes in membrane function including alteration in the sodium-potassium pump, and alteration of conductance-generating functions dependent upon membrane structure. In addition, changes in intracellular ionic concentrations relevant to cell function may be determined by clamping. The general level of cellular integrity and function can be determined best by clamping. Voltage clamp studies therefore are potentially very useful in the research of various neural diseases.

2. Description of the Prior Art

Early voltage clamp circuits employed a pair of microelectrodes which were inserted into the nerve cell under examination. A system of this type is shown in FIG. 2. The nerve cell comprises a cell body 10, dendrites 12, an axon 14 and nerve endings 16. Microelectrodes 18 and 20 are inserted through the cell membrane into the cell body. The electrode 18 is connected to voltage measurement circuitry 22 which measures the membrane potential and compares it to a command potential. An error feedback signal is generated as a function of the difference between the measured membrane potential and the command potential. The error feedback signal is used to control current injection circuitry 24, which injects current into the cell body via the electrode 20 so as to "clamp" the membrane potential to a value equal to the command potential. The amount of current necessary to achieve clamping is measured and can be used to determine conductance changes in the cell membrane.

The system shown in FIG. 2 thus utilizes separate electrodes for voltage measurement and current injection, and a continuous error feedback signal is provided. Although such a system provides very effective voltage clamping, the requirement of two electrodes makes it unusable in the study of many similar cells, particularly mammalian cells. In order to overcome this problem, voltage clamps utilizing a single electrode have been developed. In such circuits, the single microelectrode is rapidly switched from a current passing to a voltage recording mode. During a first portion of a cycle, the clamping circuitry is in a voltage recording mode and measures and stores the value of the membrane potential. The stored value is compared to the command potential. During the second half-cycle, the circuitry is switched to a current injecting mode and current is injected into the cell based upon the difference between the held value and the command potential. The single electrode clamp thus operates by providing discontinuous feedback, i.e., during the time that the membrane potential is being measured no clamping current can be injected. In order adequately to monitor the electrical activity of a cell, the clamp must be switched between the current injecting and voltage measuring modes at a rate which substantially exceeds the rates of conductance changes occuring within the cell. As can be seen in FIG. 1, conductance change which causes the membrane potential to change from the resting potential to the reversal potential can occur in a few tenths of a millisecond. In order to monitor such conductance changes, a switching frequency on the order of 100 kHz, or higher, is desirable.

Various single-electrode voltage clamps have been developed. Early clamps comprised a bridge circuit in which the cell membrane serves as an unknown resistor on one arm of a bridge. These clamps are inaccurate since the resistance of the electrode varies with current and time, thus making verification of bridge balance impossible, and thus resulting in errors in the measurement of membrane potential. A second type of single electrode clamp is disclosed in Wilson and Goldner, "Voltage Clamping With A Single Microelectrode", *Journal of Neurobiology*, Volume 6, No. 4, pages 411-422. In this circuit, the membrane potential at the output of an electrode preamplifier is sampled by sample-and-hold circuitry during periods when current injection is held to zero. The potential stored by the sample and hold is connected to a feedback circuit and compared with a command potential. During intervals of holding the membrane potential, the feedback circuit is switched to inject current based upon the difference between the held membrane potential and the command potential. The basic circuitry includes a high input impedance, low input capacity preamplifier to amplify the membrane voltage, sample-and-hold circuitry to store the amplified value, a current source to supply the necessary clamping current, a comparator for comparing the held membrane potential with the command potential and an FET switch to switch between the current injection and voltage measurement modes. Although this circuit is an improvement over the bridge-type circuit, its usefulness is limited in that its maximum switching rate is on the order of 10 kHz and minimum clamping time is greater than two milliseconds. This speed is insufficient to clamp fast events such as action potentials.

A specific preamplifier which may be used with a voltage clamp such as that disclosed in the Wilson et al. article is described in Kootsey and Johnson, "Buffer Amplifier With Femtofarad Input Capacity Using Operational Amplifiers", *IEEE Transactions of Biomedical Engineering*, Volume 20, September 1973, pages 389-391. This preamplifier provides an input capacity below 0.01 pF and an input resistance above 1012 ohms. A voltage clamp using a similar preamp is described in Merickel, "Design of a Single Electrode Voltage Clamp", *Journal of Neuroscience Methods*, 2 (1980) 87-101. This article discloses a circuit implementing the technique described in the Wilson et al. article. Since the clamping action takes about two milliseconds, this circuit is effective only for examining slow membrane activity, i.e., the circuit is too slow to be useful in the study of the action potential.

SUMMARY OF THE INVENTION

The present invention provides an improved single-electrode voltage clamp which achieves clamping in less than 100 microseconds, thus enabling the action potential of nerve cells to be studied. The circuit includes a high input impedance, low input capacitance input stage connected to the measurement electrode. A capacity neutralization network provides positive feedback to further reduce the input capacitance of the system. A high frequency equalization network is connected to the output of the input stage to provide initial modification of the signal from the input stage. Further correction is provided by separate low frequency compensation and transient compensation networks. The membrane voltage is sampled by means of a sample-and-hold network and after further filtering, the sampled value is compared to the command potential. Clamping circuitry generates a pulse output current which is delivered to the cell and causes the cell to be clamped at the command potential. A computer controlled circuit is utilized to insure that the clamp is operating properly.

BRIEF DESCRIPTION OF THE DRAWINGS

The invention will now be described with reference to the accompanying drawings wherein:

FIG. 1 is a diagram of membrane potential of a typical nerve cell.

FIG. 2 is a diagram of a prior art dual electrode voltage clamp system.

FIG. 3 is a diagram showing the basic components of the single electrode voltage clamp of the present invention.

FIGS. 4A-D show various waveforms associated with the circuit of FIG. 3.

FIG. 5 is a block diagram of the present invention.

FIGS. 8A and 8B are waveforms showing the effects of the equalization stage of the voltage clamp.

FIG. 9 is a waveform showing low frequency and high frequency aberrations which are removed by compensation networks contained in the voltage clamp.

FIG. 10 is a waveform representing an error component introduced by follower action of the voltage clamp.

FIG. 11 shows a simulated cell circuit used to tune up the voltage clamp of the invention.

FIG. 12 is a block diagram of computer correction circuitry used with the invention.

FIGS. 13A-E are waveforms associated with the computer correction.

DESCRIPTION OF THE PREFERRED EMBODIMENT

Figure 6:
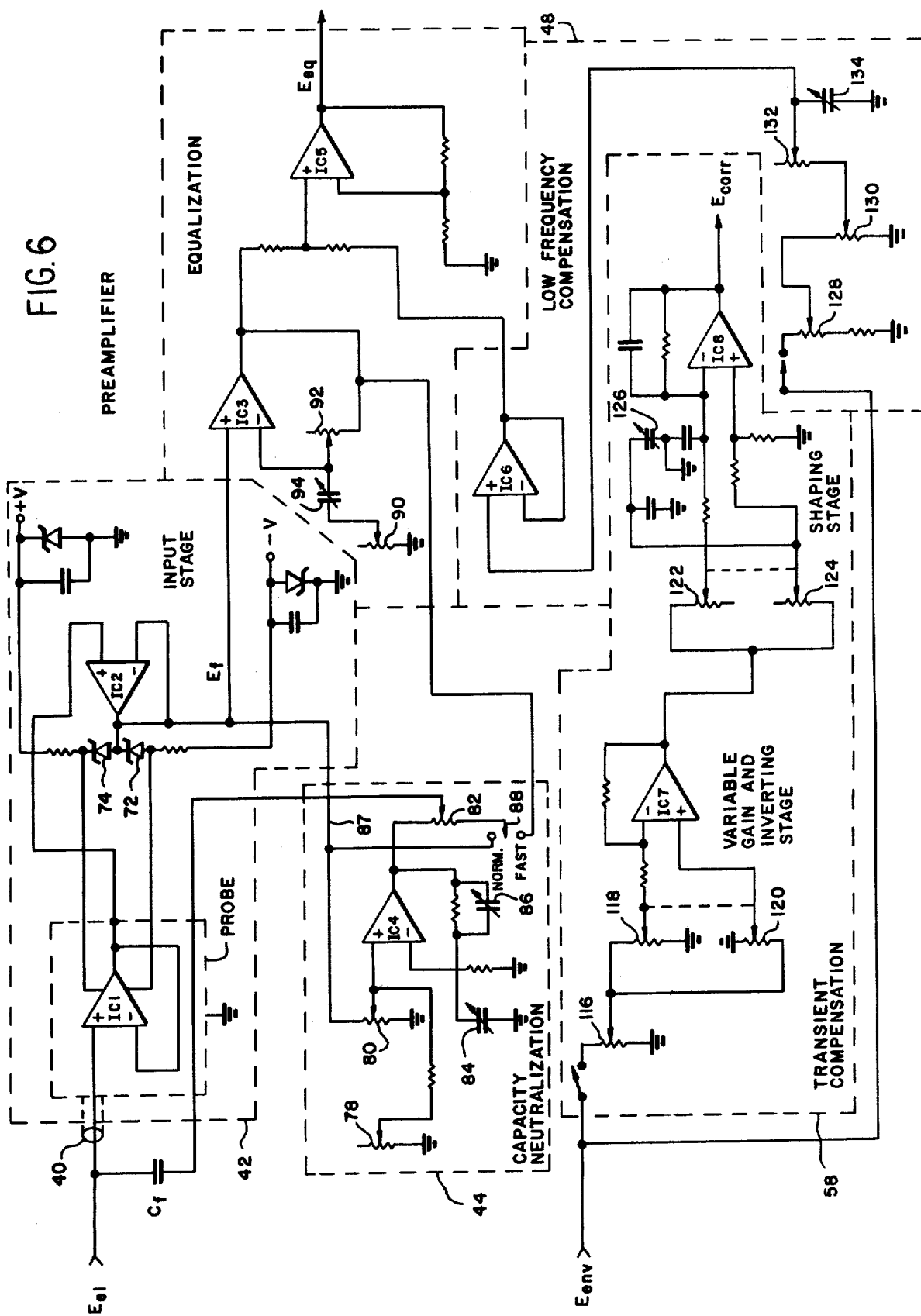
FIG. 6 is a schematic diagram of the preamplifier section of the present invention.

Referring to FIG. 3, a cell 30 is indicated as having an associated membrane resistance $R_m$, capacitance $C_m$ and potential $E_m$. An electrode 32 includes a resistance $R_e$ and an associated shunt capacitance $C_s$. The electrode 32 is connected to a voltage measurement circuit 34 which functions to measure the membrane potential $E_m$. The circuit 34 has an associated input capacitance $C_i$. The potential $E_m$ is compared to a command potential $E_{comm}$ by a clamping circuit 36 and current is injected to the electrode 32 by the clamping circuit 36 so as to make $E_m$ equal to $E_{comm}$.

The injection of current to the cell 30 is discontinuous, i.e., during the first portion of the cycle a current pulse is applied to the electrode 32 and during the second portion of the cycle, the current pulse is removed and the cell potential $E_m$ is measured. On the subsequent portion of the cycle, the current which is injected is a function of the cell potential measured in the previous portion of the cycle. The application of the current pulse charges the cell 30 to a value equal to the command potential. The time constant of the RC network of the cell is much greater than the cycling time of the clamping current, so that the pulses of current will be smoothed into a dc voltage. The cell potential $E_m$ will thus remain relatively constant at the command potential.

In addition to the charging of the cell, the RC network of the electrode as well as the input network of the voltage measurement circuit 34 will be charged by the application of the clamping current. The input to the voltage measurement circuit 34 is the voltage $E_{el}$ at the top of the electrode 32 and will therefore include the voltage across the electrode and the input network of the circuit 34. Due to the low input capacitance of the electrode system, capacitive loading is minimized. Follower action (to be described) prevents all loading through $R_s$. An equalization circuit ($IC_3$, to be described) decreases the effective fall time of the preamplifier signal so as to allow extraction of the value (sampled at the appropriate instant, to be described) which equals $E_m$.

Referring to FIG. 4A, a typical command potential may be a 1 kHz square wave, i.e., it is desired that the cell 30 be clamped to follow the command potential waveform. The voltage $E_{el}$ at the top of the electrode 32 is the input to the voltage measurement circuit 34. The waveform of this voltage is shown in FIG. 4B. The cycling frequency, i.e., the frequency of switching between the voltage measurement and current injection modes, is shown as being 100 kHz. During the time when current is being injected into the cell, the voltage $E_{el}$ will be determined by the input to the voltage measurement circuit, the voltage across the electrode 32 and the voltage across the cell 30. When the current is removed during the voltage measurement portion of a cycle, the voltages of the input network and the electrode will quickly decay, with the result being that $E_{el}$ will approach $E_m$. At this point, the voltage measurement circuitry 34 sampls the voltage $E_{el}$ (after being subjected to equalization as discussed subsequently) and provides it to the clamping circuit 36 for comparison with the command potential $E_{comm}$. Because of the long time constant of the cell 30 with respect to the cycling frequency, the voltage $E_m$ will remain relatively constant, as shown in FIG. 4C.

In order to be able to study the action potential of a cell, the cycling frequency of the voltage clamp must be much higher than the maximum frequencies of the action potential. Since the action potential may occur in under 0.5 millisecond, a cycling frequency of at least 100 kHz is necessary. Because of the capacitances of the electrode and input network to the voltage measurement circuit 34, prior art circuits have been limited to a cycling rate of approximately 10 kHz. That is, accurate measurements of the membrane potential cannot be made at cycling rates higher than approximately 10 kHz. The present invention is designed to enable a cycling rate of at least 100 kHz to be utilized and clamping is achieved in less than 100 microseconds. Changing the command potential shown in FIG. 4A may initiate conductance changes that would otherwise give rise to an action potential in a cell. In order to study the action potential, therefore, the clamp must be able to follow the fastest cellular events that result from changes in the command potential.

FIG. 5 is a block diagram of the voltage clamp of the present invention. The electrode 32 is connected via a shielded cable 40 to an input stage 42. The input stage is designed to have very high input impedance and low input capacitance so as to result in the lowest possible time constant. A capacity neturalization feedback circuit 44 is connected to the output of the input stage to provide positive feedback through capacitor $C_f$ so as to further reduce the effective $C_s$. The output of the input stage, designated $E_f$ or E follower, is fed to an equalization network 46. Ideally, the signal $E_f$ equals $E_{el}$ and the signal $E_m$ during the voltage measurement interval. Due to residual capacitive effects, however, the tracking is still not completely accurate. The equalization network 46 provides high frequency emphasis which compensates for remaining inaccuracies in the signal $E_f$ caused by the shunt capacitance $C_s$. The output of the equalization network 46 is combined with a signal from a low frequency compensation network 48 (the operation of which will be described subsequently) in a summing amplifier 49. The output of the summing amplifier is referred to as $E_{eq}$. The signal $E_{eq}$ is sampled by a sample-and-hold network 50 in order to obtain a signal $E_m$ representing the membrane potential. The sample-and-hold is controlled by means of a timing signal which causes sampling to occur during periods when no clamping current is being injected and after the voltage across the electrode and input RC networks has decayed. Thus, the sample and hold circuit 50 receives the electrode voltage as represented by the signal $E_{eq}$ and samples it at points when no current is being injected in order to determine the membrane potential $E_m$.

The sampled membrane voltage $E_{mem}$ is amplified by an amplifier 56, which also receives a compensating signal $E_{corr}$ from a transient compensation network 58 (the operation of which will be described subsequently). The output of the amplifier 56 is connected to a second sample and hold circuit 59. The held signal is modified in frequency response by means of a spectral modification circuit 60 which in the present embodiment includes an audio graphic equalizer. The spectral modification circuit provides a smoothing function to correct for frequency response and phase aberrations in the system.

The output of the spectral modification circuit 60, i.e., the modified membrane voltage, is compared to the command potential by means of a feedback amplifier 62. The command potential is multiplied by an amount equivalent to the amplification factor of the membrane potential and is modified in frequency response by a spectral modification circuit 64. The output $E_{env}$ of the feedback amplifier 62 represents the difference between the measured membrane voltage and the command potential. This output is an envelope of the current to be injected to the cell. During periods of current injection, an electronic switch 66 is closed and the error signal $E_{env}$ is connected to an output amplifier 68, which provides a clamping current to the electrode (and cell) through a series resistor $R_s$. During the voltage measurement cycle, the signal $E_f$ is connected to the output amplifier 68 so that it acts as a follower, thereby preventing any discharge from occuring through the resistor $R_s$. The current through the resistor $R_s$ is monitored by means of an amplifier 70.

Referring now to FIG. 6, a more detailed circuit description of the preamplifier section of the voltage clamp is shown. The input stage 42 of FIG. 5 includes two integrated circuits IC1 and IC2 as well as zener diodes 72 and 74. The operation of the input stage is similar to that described in the Kootsey and Johnson article. The IC1 package (designated as a "probe" in FIG. 6) is connected to a power supply which follows the input voltage to IC1. As the input voltage varies, IC2 will be driven so as to control the application of positive and negative supply voltages $+V$ and $-V$ to IC1. In this manner, the effective input capacitance of the input stage can be reduced to an extremely low level.

In order to compensate for the shunt capacitance $C_s$ of the electrode, the positive feedback capacity neutralization network 44 is employed. Without capacitive feedback, the output $E_f$ of the input stage 42 would appear as shown in FIG. 4B. The major drawback of this signal is that its rise time, indicated generally at 76, is quite slow. This slow response to the step change in injected current is caused by the electrode shunt capacitance $C_s$. The capacity neutralization circuit 44 provides positive feedback which neutralizes the shunt capacitance $C_s$. The neutralization circuit includes amplifier IC4, potentiometers 78, 80 and 82, and variable capacitors 84 and 86. The circuit operates as a high frequency emphasis amplifier, and the variable components are adjusted to reduce capacitive aberrations in $E_f (=E_{el})$. This adjustment may be accomplished by means of visual observation of the output of the input stage ($E_f$) on an oscilloscope. With the application of positive feedback provided by the capacity neutralization network 44, the output $E_f$ will have an appearance as shown in FIG. 4D. In order to increase stability, a portion of $E_f$ is normally fed back directly to the input via line 87 through switch 88. The switch 88 may be moved to a "fast" position in order to provide even faster rise time in $E_f$, albeit with a decrease in stability. In this position, a signal from the equalization network is fed back to the input.

The output $E_f$ of the input stage is coupled to the equalization network 46, which includes a pair of integrated circuits IC3 and IC5, as well as potentiometers 90 and 92 and variable capacitor 94. Whereas the capacity neutralization network compensates for low frequency problems caused by the shunt capacitance $C_s$ (e.g., the slow response to a step in the command potential), the equalization network is designed to compensate for high frequency aberrations caused by the shunt capacitance. The equalization network will improve the system response with respect to the 100 kHz square wave cycling frequency. The signal $E_f$ will have an appearance as shown in FIG. 8A. Although the response to the step change in the command potential was increased by the capacity neturalization network, the response of the amplifier to a 100 kHz square wave is still quite slow. The equalization network 46 provides high frequency emphasis which serves to increase the response speed to the the 100 kHz square wave. The improved response (the signal $E_{eq}$) is as shown in FIG. 8B. The equalization network 46 provides a signal which falls to a level which is much closer to $E_m$ than is the signal $E_f$. As is the case with the capacity neutralization network, the variable components of the equalization network are adjusted while the output $E_{eq}$ is viewed on an oscilloscope in order to achieve the best response. It is noted that the equalization circuit does not provide feedback to the preamp input, but rather a direct alteration of the waveform $E_f$.

Figure 7:
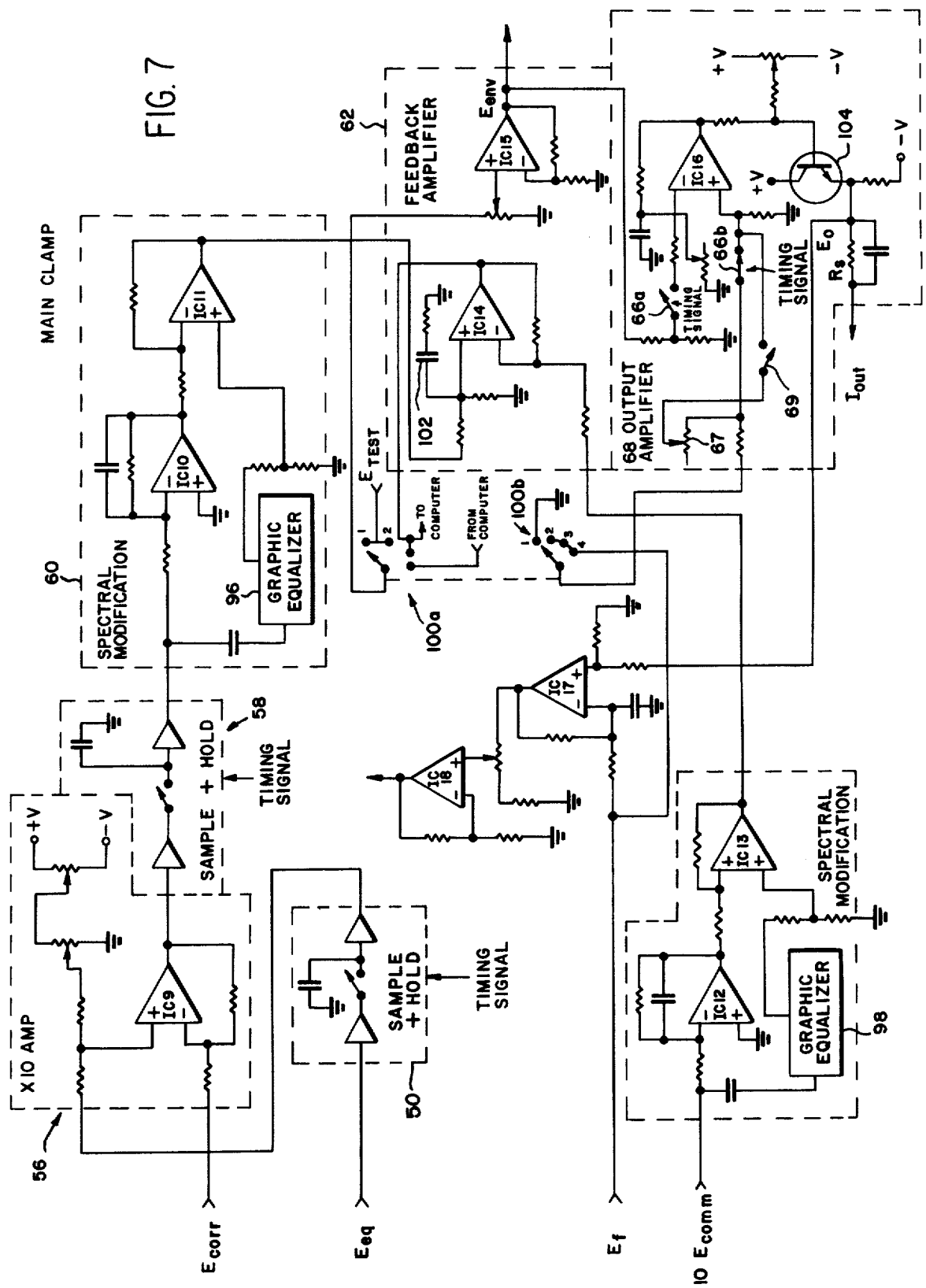
FIG. 7 is a schematic diagram of the sampling and clamping circuitry of the present invention.

Referring now to FIG. 7, the output $E_{eq}$ of the equalization network is sampled by the first sample-and-hold circuit 50. The sample point is controlled by a timing signal so as to occur during the time period when no current is being injected into the cell. The specific timing of the timing signal is adjustable to enable sampling to be done at the point of minimum aberration of the signal $E_{eq}$. The output $E_m$ of the sample-and-hold circuit 50 is a representation of the potential of the cell membrane. This signal is fed to the gain ten amplifier 56, which includes IC9. It is at this point that a signal $E_{corr}$ from the transient compensation network is subtracted from the signal $E_{eq}$. The amplified membrane potential is sampled by the second sample-and-hold circuit 58, the reason for which will be discussed subsequently.

The membrane potential signal which is held by the sample-and-hold circuit 58 has some degree of instability. The spectral modification circuit 60 is included to smooth the response of the held signal. The spectral modification circuit includes a graphic equalizer 96 which operates on frequencies between 500 Hz and 10 kHz. In the present embodiment, the graphic equalizer is an octave equalizer, although an equalizer with one-third octave controls can be utilized. Signals below 500 Hz are passed unequalized through an amplifier including IC10 and are recombined with the equalized signals at IC11. The proper settings for the graphic equalizer 96 are determined by viewing the clamped cell potential on an oscilloscope.

The output of the spectral modification circuit 60 is compared to the equalized command potential at IC14. The command potential signal is passed through a spectral modification unit 64 which includes a graphic equalizer 98 and integrated circuits IC12 and IC13 which perform functions identical to the equalizer 96 and IC10 and IC11, respectively. After the setting of the equalizer 96 is fixed, the equalizer 98 is adjusted in order to minimize overshoot and ringing in the controlled membrane signal when the command potential changes. The output of IC14 is an error signal representing the difference between the command potential and the actual membrane potential. When a switch 100a is in position three, the output of IC14 will be coupled to an op amp IC15. IC14 and IC15 comprise a two stage amplifier having a gain of approximately three hundred. The output of IC15 is the error signal $E_{env}$. This signal is periodically connected to the output amplifier section 68 through the electronic switch 66a. The output amplifier includes an integrated circuit IC16 as well as an emitter follower 104. The follower 104 provides a low impedance isolated output signal Iout, which is the current to be injected to the electrode, i.e., the current which passes through $R_s$. IC17 and IC18 monitor the current through $R_s$ by comparing the output of the follower 104 with $E_f$ (which should be equivalent to $E_{el}$). The output of IC17 is coupled to IC18, the output of which is a signal representing the current passing through $R_s$, i.e., the current injected to the electrode.

Thus, clamping current is injected to the electrode through the series resistor $R_s$. During the voltage measurement cycle, current leakage from the cell back through $R_s$ must be prevented in order to obtain optimum performance. In order to accomplish this, the output voltage $E_f$ of the input stage is fed to the output amplifier 68 during the voltage measurement cycle, i.e., the circuit operates as a follower. As shown in FIG. 7, the signal $E_f$ is passed through a switch 100b and through an electronic switch 66b to IC16. The switch 66b is closed during the voltage measurement interval, whereas the switch 66a is closed during the current injection interval. Thus, during voltage measurement the output of IC16 is equal to $E_f$. Since $E_f$ is essentially equal to $E_{el}$, the voltage across $R_s$ during the voltage measurement cycle will be 0 and no current will leak through $R_s$. It should be noted that during current injection, a small amount of the signal Ef is coupled to IC16 through potentiometer 67 and switch 69. This provides additional stability to the operation of the system.

The initial tune-up procedure, i.e., the adjustment of the capacity neutralization and equalization circuits, is accomplished without the follower connected, i.e., with the switch 100b in position 1 (the follower is grounded). Rough tune-up, which is less dependent upon electrode parameters, is more easily accomplished in this manner. However, when the follower is activated, the discharge characteristics of $E_{el}$, and therefore $E_f$, will be changed since the discharge path through $R_s$ is eliminated. That is, the addition of the follower action results in a transformation of the signal $E_f$. The purpose of the low frequency compensation circuit 48 and transient compensation circuit 58 is to compensate for the transformation of $E_f$ occurring by the addition of the follower. Thus, the clamp circuit is initially tuned up without the follower connected and additional circuitry is included to compensate for changes in the circuitry operation caused by the addition of the follower.

The output $E_{env}$ of the feedback amplifier 62 (output of IC15) is an envelope of the current to be injected to the electrode. This signal is also utilized to generate the correction signals to compensate for the effects of the follower. The connection of the follower to the circuit results in a high frequency aberration and low frequency aberration in the measured membrane potential. As shown in FIG. 9, the output $I_{out}$ (at 104) will be a waveform 108 having a high frequency aberration 110 and low frequency aberration 112 which aberrations also appear in $E_f$, and therefore, in $E_{eq}$. After equalization and subsequent spectral modification by the circuit 60, this signal is compared to the output of the spectral modification circuit 64. The resulting signal for $E_m$ will be as indicated in FIG. 10, and includes the low frequency and high frequency aberrations. The function of the compensation circuits 48 and 58 is to generate inverse signals to counteract the effects of the follower. The transient compensation circuit 58 includes integrated circuits IC7 and IC8, potentiometers 116–124 and variable capacitor 126, as well as other fixed value components. The function of this circuit is to generate a high frequency spike of controlled amplitude and duration. The variable components are adjusted until the shape of the spike corresponds to the spike 110 in FIG. 10. The output $E_{corr}$ of the transient compensation circuit is fed back at the gain ten amplifier 56 (at IC9 in FIG. 7). A separate low frequency compensation circuit is included to eliminate the low frequency aberration of FIG. 10. This circuit includes IC6, potentiometers 128–132 and variable capacitor 134. The low frequency compensation circuit 48 operates essentially as a low pass filter, and the output of IC6 is added to the equalization stage at IC5. The operation of the transient compensation and low frequency compensation circuits thus serves to restore the membrane potential waveform to its correct shape.

The second sample-and-hold circuit 58 is included in order to isolate the transient correction signal $E_{corr}$ from the remainder of the circuit during voltage measurement. Otherwise, $E_{corr}$ could potentially affect the follower action during the voltage measurement interval. This isolation improves stability and reduces output aberrations.

The switches 100a and 100b of FIG. 7 are used to control the various stages of tune-up of the system. Initially, the switches are in position one. In this position, the follower circuit is not connected and a rough tune-up procedure conducted. During this procedure, the input stage 42, capacity neuralization circuit 44 and equalization circuit 46 can be adjusted to achieve best response. This initial phase of the tune-up procedure is accomplished by means of a simulated cell circuit as shown in FIG. 11. The resistance R1 (141) is chosen at approximately 20 megohms to simulate the electrode resistance $R_{el}$, while resistor 142 is chosen at approximately 5 megohms to simulate the resistance of the membrane $M_{mem}$. A test signal $E_{test}$ is arbitrarily a square wave at approximately 3 kHz and represents a simulated cellular potential to be clamped and IC 144 is a follower amplifier to buffer the simulated membrane potential ($E_{sim}$) for observation on an oscilloscope.

Initially a switch S is closed to ground the "tip" of the simulated electrode. Switch 100 is placed in position 1, and a 1 kHz square wave is applied at the noninverting input of amplifier 62 (FIG. 5). $I_{out}$ will then consist of a 100 kHz signal whose envelope will be the 1 kHz square wave. With these conditions, the capacity neutralization and equalization circuits can be adjusted by direct observation of the signal at the output of IC3, so that $E_{eq}$ will have the proper waveform to produce essentially zero output for $E_{mem}$ when sampled by the first sample-and-hold circuit 50. Using this procedure makes adjustment of the input system relatively independent of electrode parameters.

Once the input circuits have been correctly adjusted, the switch S may be opened. The low frequency and transient compensation networks can then be coarsely adjusted so that the 10 $E_{mem}$ signal has essentially the same waveform as $E_{sim}$, observed on an oscilliscope when the follower is turned on (switch 100 in position 2).

After the above adjustments are complete, clamping adjustments can be performed. Fine adjustment of the spectral modification circuits 60 and 64, and, again, of the low frequency and transient compensation circuits 48 and 58 may be completed by simultaneously observing $E_{sim}$ and 10 $E_{mem}$ while a square wave at $E_{comm}$ (at 1 kHz) is applied. When these adjustments are completed, aberrations should be reduced to less than 100 microseconds.

Through appropriate switching circuitry, the clamp may then be connected to an actual electrode system which is similar to that described above, but which includes an actual microelectrode to be used in the neuron to be studied. Fine tuning of the clamp can then be achieved prior to cell impalement. Further varification of clamp operation, after cell impalement, is attained by computer-directed control circuitry described below.

Due to the large amount of signal manipulation provided by the clamp circuitry, it is necessary to verify that the membrane potential which is derived during the accomplished by means of computer control. A computer is utilized to smoothly disengage the clamp for a short period of time (e.g., on the order of a millisecond). A check for a discontinuity in the measured membrane potential during disengagement of the clamp is made. The membrane potential will not change abruptly with the disengagement of the clamp. Therefore, if the circuit is operating properly, the calculated or derived membrane potential will not change abruptly as the clamp is disengaged (although the potential may change relatively slowly due to cell activity). The computer operates to ensure that the disconnection will occur in an orderly fashion and avoids any mechanical switch activity that could cause disturbance in the cell.

Referring to FIG. 12, the output of IC14 is delivered via switch 100a (when in position 4) to an analog multiplier 120 as signal $M_1$. A second input $M_2$ to the multiplier 120 is provided by a computer 122. The output of the multiplier is delivered back to the switch 100a (and subsequently IC15) through an amplifier 124. The input to IC15 thus becomes the instantaneous product of the output $M_1$ of IC14 and a computer-derived parameter $M_2$. The gain of the feedback loop of the clamp circuit is therefore under control of the computer. The purpose of the computer loop is to allow for adjustment of the clamp gain so as to provide orderly and rapid disengagement of the clamp. Once the clamp is disengaged (i.e., the main feedback loop is deactivated), the follower remains on (switch 100b is closed) and current injection is thus held to zero. Any discontinuity in the derived membrane potential or injected current will indicate improper operation of the clamping circuit. This will be the case even if an action potential occurs during disengagement, since changes caused by the action potential will occur in a smooth fashion compared to changes resulting from incorrect $E_m$ measurement.

The shape of the disengaging signal $M_2$ is somewhat critical because of the transients which can be reflected in the $E_{mem}$ processing circuitry with excessively rapid changes in feedback gain. The form of the disengagement signal is constant, however, and is stored in the computer memory as part of the operating program. In the present embodiment, the computer provides a signal $M_2$ which decays in an approximately exponential fashion. Exact parameters of the exponential function are determined by observing the disengagement response in the simulated circuit prior to studying the actual cell. The computer could also be programmed to provide different disengagement signals, as will be apparent to those skilled in the art. The critical factor is to provide a disengagement signal which results in smooth disengagement of the clamp. The computer 122 thus operates to provide a controlled disengagement signal to the feedback system to reduce feedback gain to zero, thus disengaging the clamp.

In addition to the checking feature, the computer 122 is also utilized to provide a final correction signal to eliminate a short transient (on the order of 100 microseconds) in the measured membrane potential. Referring to FIG. 13A, the membrane potential resulting from an abrupt change in cell current (such as is caused by a stimulus in the form of a step change in command position) is shown. As shown in FIG. 13D, however, the circuit response to the change in cell potential includes a transient 128 of approximately 100 microseconds duration. This error transient cannot be further corrected in the clamp circuit without encountering problems of ringing and oscillation. The computer 122 operates to generate error correction signals $M_3$ and $M_4$ which are injected so as to practically eliminate the error transient 128.

The computer correction operates upon the physiologically reasonable assumption that the parameters of the cell will not change significantly from stimulus to stimulus (for several successive stimuli) and that the error transients generated by the circuit will therefore be similar in response to successive stimuli. The computer operates to store the error in the measured membrane potential during one stimulus, and during a subsequent stimulus computer-derived correction signals are inserted so as to cancel the transient error. The correction signal $M_4$ is shown in FIG. 13C. The signal $M_3$ in FIG. 13B is shown as being constant; however, it may be necessary to vary this parameter in particular cases of cellular function, i.e., to compensate for known and predictable changes in cell response to successive stimuli).

Referring to FIG. 13, the measured membrane potential, represented by a signal $E_{memd}$ is fed to a digitizer 130, whose output is connected to the computer 122. The signal $E_{memd}$ is a combination of the signal $E_{mem}$ from the sample and hold circuit 50 and the signal 10 $E_{mem}$ from the amplifier 56. These signals are combined in a potentiometer 132 and amplified by a circuit 134, which includes some frequency compensation. The combined signal $E_{memd}$ is a better approximation of the actual membrane response because the early transients in the 10 $E_m$ and $E_m$ signals are in opposite directions due to the splitting of the high frequency and low frequency compensation signals. The actual membrane potential is thus better respresented by the combined signal $E_{memd}$. Based upon the input received from the digitizer 130, the computer 122 generates the correction signals $M_3$ and $M_4$. In the present embodiment, the correction signal begins a short time before the occurrence of a stimulus (i.e., a change in the command potential). The effects of the computer correction are shown in FIGS. 13D and 13E. Whereas without computer correction the injected current has a relatively slow rise and fall time, the computer correction provides faster rise time without degrading the stability of the circuit. This computer correction enables clamping to be achieved in substantially less than 100 microseconds.

In summary, the present invention provides a voltage clamp which includes various correction and compensation circuits to significantly increase clamping speed. In addition, computer controlled circuitry is employed to provide both correction and checking features. The circuit can achieve clamping in substantially less than 100 microseconds, thereby enabling action potentials to be studied.

I claim:

1. In a single electrode voltage clamp used to study neuronal cells, said clamp including voltage measurement circuitry for determining the membrane potential of a cell during a measurement interval and feedback circuitry for comparing the determined membrane potential with a command potential and injecting current into the cell during a current injection interval as a function of the difference between the membrane potential and command potential, wherein the value of command potential varies at a relatively low cell frequency and switching between voltage measurement and current injection occurs at a much higher frequency, wherein the voltage measurement circuitry includes an input section for amplifying the output of the electrode, the improvement for increasing the speed of the clamp circuit comprising capacitance compensation means for separately minimizing both low frequency and high frequency response aberrations of the input section caused by shunt capacitance of the electrode.

2. The voltage clamp of claim 1 wherein the capacitance compensation means includes positive feedback means for providing negative capacitance to the input of the input section, said positive feedback means including variable means for controlling the amount of feedback in the low frequency spectrum.

3. The voltage clamp of claim 2 wherein the positive feedback means comprises a high frequency emphasis amplifier.

4. The voltage clamp of claims 1 or 2 wherein the capacitance compensation means includes equalization means, connected to the output of the input section, for minimizing high frequency response aberrations in the output of the input stage.

5. The voltage clamp of claim 4 wherein the equalization means comprises a high frequency emphasis amplifier.

6. The voltage clamp of claim 2 wherein the low frequency spectrum is centered at about 1 kHz and the high frequency spectrum is centered above 100 kHz.

7. A single electrode high speed voltage clamp circuit for clamping the membrane potential of a cell to a predetermined command potential, comprising:
  voltage measurement means for determining the membrane potential during a voltage measurement interval, said means including a preamplifier section having an input stage for receiving the output of an electrode and a sample and hold section for sampling the output of the preamplifier section at predetermined time intervals, wherein the sampled output represents the membrane potential of the cell;
  clamping circuitry including feedback means for comparing the output of the sample and hold section with the command potential and output means for injecting current into the cell during a current injection interval which alternates with the voltage measurement interval, wherein the injected current is a function of the output of the feedback means;
  follower means for connecting the output of the input stage to the output means during the voltage measurement interval to thereby prevent current leakage from the electrode through the output means, wherein the voltage measurement means is initially tuned with the follower means disconnected to reduce the effects of variations in electrode parameters; and
  compensation means, connected to the feedback means, for correcting response aberrations in the voltage measurement means caused by the connection of the follower means.

8. The voltage clamp of claim 7 wherein the voltage measurement interval is less than five microseconds.

9. The voltage clamp of claim 7 wherein the compensation means includes separate low frequency and transient compensation means for eliminating relatively low frequency and high frequency response aberrations, respectively.

10. The voltage clamp of claim 9 wherein the low frequency compensation means comprises a first amplifier which receives the output of the feedback means and introduces a variable high frequency rolloff thereto, wherein the output of the first amplifier is fed back to the voltage measurement means.

11. The voltage clamp of claim 10 wherein the output of the first amplifier is fed back to the preamplifier section.

12. The voltage clamp of claims 9 or 10 wherein transient compensation means comprises an amplifier which receives the output of the feedback means and generates an output which is a transient having variable amplitude and width, which is fed back to the voltage measurement means.

13. The voltage clamp of claim 12 wherein the output of the transient compensation means amplifier is connected to the sample-and-hold section.

14. A single electrode voltage clamp for clamping the membrane potential of a cell to a predetermined command potential, comprising:
  current injection means for injecting current into a cell through an electrode during a current injection interval;
  voltage measurement means, adapted for connection to the electrode, for determining the membrane potential of the cell during a measurement interval which alternates with the current injection interval and for comparing the determined membrane potential with the command potential to generate a feedback signal which controls the amount of current injected into the cell, wherein a sudden change in cell current will cause the voltage measurement means to generate a transient which is not an accurate representation of the actual membrane potential; and
  computer controlled correction means, connected to the voltage measurement means, for generating a correction signal in response to the generation of a transient and applying the correction signal to the voltage measurement means to eliminate a transient generated in response to a sudden change in cell current.

15. The voltage clamp of claim 14 wherein the voltage measurement means includes feedback means for generating the feedback signal and wherein the correction signal is applied to the feedback means.

16. The voltage clamp of claim 14 wherein the correction means generates a correction signal in response to the generation of a first transient and later applies the correction signal to eliminate a subsequent transient.

17. The voltage clamp of claim 15 wherein the command potential includes arbitrary changes which cause the current injection means to inject current which results in a sudden change in cell current, wherein the computer correction means is controlled so that the correction signal is applied to the feedback means to coincide with a subsequent change in the command potential.

18. The voltage clamp of claim 17 wherein the correction signal is applied to the feedback means beginning just prior to the occurrence of a step in the command potential.

19. A single electrode voltage clamp for clamping the membrane potential of a cell to a predetermined command potential, comprising:
  current injection means for injecting current into a cell through an electrode during a current injection interval;
  voltage measurement means, adapted for connection to the electrode, for determining the membrane potential of the cell during a voltage measurement interval which alternates with the current injection interval;
  feedback means for comparing the output of the voltage measurement means with the command potential and controlling the amount of current which is injected by the current injection means; and
  verification means for insuring that the output of the voltage measurement means is an accurate representation of the actual membrane potential, said verification means including control means for causing the output of the feedback means to smoothly and quickly fall to zero, whereby a discontinuity in the output of the voltage measurement means indicates improper operation of the voltage clamp.

20. The voltage clamp of claim 19 wherein the control means comprises computer control means for generating a control signal to be combined with a signal from the feedback means, wherein the control signal controls the gain of the feedback means.

21. The voltage clamp of claim 20 wherein the computer control means generates a signal which approximately exponentially falls to zero.

22. A single electrode high speed voltage clamp for clamping the membrane potential of a cell to a predetermined command potential, comprising:
   a low input capacitance input stage means for receiving an input signal from an electrode, said input stage means providing an output signal which tracks the input signal;
   capacity compensation means connected to the input stage to compensate for shunt capacitance of the electrode;
   sample and hold means for sampling the output of the capacity compensation means in response to a control signal;
   feedback means for comparing the output of the sample-and-hold means with the command potential;
   output means for injecting a clamping current into a cell through the electrode;
   switching means for connecting the output of the feedback means to the output means during a current injection interval and for connecting the output of the input stage means to the output means during a voltage measurement interval so that the output means acts as a follower to thereby eliminate any current leakage through the output means during the voltage measurement interval, wherein the sample-and-hold means samples during the voltage measurement cycle and wherein initial adjustment of the capacity compensation means is performed without the follower connected;
   follower compensation means for providing one or more correction signals to the sample-and-hold means to correct for inaccuracies in the output of the capacity compensation means caused by connection of the output means as a follower; and
   computer correction means, connected to the sample and hold means, for removing transients from the output of the feedback means caused by a sudden change in cell current.

23. The voltage clamp of claim 22 wherein the sample and hold means includes spectral modification means for controlling the frequency response of the sampled signals to thereby increase the stability of the clamp.

* * * * *